US009506457B2

(12) United States Patent
Kirkpatrick

(10) Patent No.: US 9,506,457 B2
(45) Date of Patent: Nov. 29, 2016

(54) CONTACTLESS FLUID PUMPING METHOD AND APPARATUS

(75) Inventor: Gregg Rodne Kirkpatrick, San Diego, CA (US)

(73) Assignee: CAREFUSION 303, INC., San Diego, CA (US)

(*) Notice: Subject to any disclaimer, the term of this patent is extended or adjusted under 35 U.S.C. 154(b) by 626 days.

(21) Appl. No.: 12/896,758

(22) Filed: Oct. 1, 2010

(65) Prior Publication Data

US 2012/0083759 A1 Apr. 5, 2012

(51) Int. Cl.
| F04B 11/00 | (2006.01) |
| F04B 43/04 | (2006.01) |
| A61M 5/142 | (2006.01) |

(52) U.S. Cl.
CPC ........... *F04B 11/0041* (2013.01); *A61M 5/142* (2013.01); *F04B 43/04* (2013.01); *A61M 5/14224* (2013.01)

(58) Field of Classification Search
CPC .... F04B 45/041; F04B 43/04; F04B 45/047; F04B 43/023; F04B 11/0041; F04B 11/0058; F04B 43/046; A61M 5/14224
USPC .................. 417/412, 413.1, 413.2, 474, 420, 417/477.11, 53; 251/65, 129.17, 331
See application file for complete search history.

(56) References Cited

U.S. PATENT DOCUMENTS

| 4,204,538 A | * | 5/1980 | Cannon .......................... 604/246 |
| 4,498,850 A | * | 2/1985 | Perlov et al. ................. 417/322 |
| 4,519,792 A | | 5/1985 | Dawe |
| 4,541,429 A | * | 9/1985 | Prosl et al. .................... 604/249 |
| 4,790,937 A | * | 12/1988 | Eilers ........................ 210/321.71 |
| 5,011,380 A | * | 4/1991 | Kovacs ....................... 417/413.1 |
| 5,249,932 A | * | 10/1993 | Van Bork ...................... 417/386 |
| 5,599,174 A | * | 2/1997 | Cook et al. ................. 417/413.1 |
| 6,517,329 B2 | * | 2/2003 | Shiomi et al. ............. 417/413.1 |
| 6,877,713 B1 | * | 4/2005 | Gray et al. ........................ 251/7 |
| 7,271,563 B2 | * | 9/2007 | Yoo et al. ...................... 318/632 |
| 2004/0219041 A1 | * | 11/2004 | Rijnberg ........................ 417/416 |
| 2006/0009739 A1 | | 1/2006 | Poutiatine et al. |
| 2008/0240942 A1 | * | 10/2008 | Heinrich et al. ............... 417/322 |
| 2009/0209945 A1 | | 8/2009 | Lobl et al. |
| 2011/0274566 A1 | * | 11/2011 | Amirouche ....... A61M 5/14224 417/322 |

OTHER PUBLICATIONS

International Search Report and Written Opinion for PCT/US2011/052654 mailed Apr. 26, 2012 in 11 pages.

* cited by examiner

*Primary Examiner* — Devon Kramer
*Assistant Examiner* — Kenneth J Hansen
(74) *Attorney, Agent, or Firm* — McDermott Will & Emery LLP

(57) ABSTRACT

A fluid pump apparatus for pumping a fluid from a fluid source to a fluid output comprises a first portion, such as a durable portion, and a second portion, such as a disposable portion. The first portion includes a fluid chamber having a wall and an internal cavity, an input port and an output port. A membrane forms a portion of the wall. The first portion further includes a magneto-sensitive element coupled to the membrane. The second portion comprises an actuator configured to contactlessly induce a reciprocating movement of the membrane by application of a time-varying magnetic field to the magneto-sensitive element, thereby facilitating pumping of the fluid through the fluid chamber.

7 Claims, 8 Drawing Sheets

CONTACTLESS FLUID PUMPING METHOD AND APPARATUS

FIELD

The present disclosure relates, in general, to a fluid delivery system, and more particularly, to a contactless fluid pump.

BACKGROUND

Fluid delivery pumps are commonly used in, for example, patient care systems for infusing medication to a patient or for clinical testing and experimentation purposes. A variety of mechanized fluid delivery system designs are known in the art. Generally speaking, these designs combine a valve mechanism to sequester the flow in one direction (e.g., towards a fluid source) and a pump mechanism to deliver the flow in the other direction (e.g., towards a patient). The fluid being delivered is contained within a disposable portion that is fluidly isolated from a durable portion that delivers the pumping force.

Conventional mechanized fluid delivery systems suffer from certain operational setbacks. For example, fluid delivery is often noisy due to the movements of mechanized parts. Furthermore, because the pumping action is achieved by physical contact between the disposable portion and a pumping element of the durable portion, the risk of undesirable contamination of the durable portion due to leakage of medical fluid from the disposable portion exists. Also, due to mechanical wear and fatigue, fluid delivery systems often cannot be put into continuous use for a long period (e.g., greater than 96 hours run time). In certain patient care situations, it is undesirable or cumbersome to change fluid delivery equipment during long fluid delivery sessions. Furthermore, the amount of fluid pumped in each stroke in a conventional mechanized fluid delivery system cannot be changed while fluid delivery is ongoing.

There is a need for a better fluid delivery system that addresses one or more of these concerns. This and other needs are met by contactless fluid pumping methods and apparatuses disclosed in the present disclosure.

SUMMARY

According to certain exemplary aspects, a fluid pump apparatus for pumping a fluid from a fluid source to a fluid output is disclosed. A first portion comprises a fluid chamber having a wall and an internal cavity, an input port and an output port. The first portion further includes a membrane forming a portion of the wall and a magneto-sensitive element coupled to the membrane. A second portion comprises an actuator configured to contactlessly induce a reciprocating movement of the membrane by application of a time-varying magnetic field to the magneto-sensitive element, thereby facilitating pumping of the fluid through the fluid chamber.

According to certain exemplary aspects, a method of pumping a fluid from a fluid source to a fluid output is disclosed. A pump portion is connected to the fluid source, the pump portion having a fluid chamber coupled to a magneto-sensitive element, with a volume of the fluid chamber dependent on a position of the magneto-sensitive element. A reciprocating movement is induced in the magneto-sensitive element contactlessly to vary the volume of the fluid chamber, thereby causing the fluid to pump from the fluid source to the fluid output.

According to still other exemplary aspects, a disposable apparatus for use in a fluid pump system is disclosed. A fluid chamber has a wall, an internal cavity, an input port and an output port. A membrane forms a portion of the wall. A magneto-sensitive element is coupled to the membrane such that a reciprocating movement of the magneto-sensitive element in response to an external magnetic field causes the membrane to reciprocate, thereby facilitating pumping of a fluid through the fluid chamber.

In further exemplary aspects, a disposable apparatus for use in a fluid pump system is disclosed. A first magneto-sensitive element is positioned at a fluid output port and a second magneto-sensitive element is positioned at the fluid output port. The first and the second magneto-sensitive elements are positioned to fluidly close the output port in a normal position and fluidly open the output port when an external magnetic field is applied to the disposable apparatus.

The foregoing and other features, aspects and advantages of the embodiments of the present disclosure will become more apparent from the following detailed description and accompanying drawings.

DETAILED DESCRIPTION

The systems and methods disclosed in the present application meet one or more of the above-discussed and other concerns related to fluid pumping systems and provide a fluid pump operable using a time-varying magnetic field.

Briefly and in general terms, certain embodiments provide a fluid pump apparatus comprising a first portion (e.g., a pump portion or a disposable portion) and a second portion (e.g., a durable portion) separable from the first portion. In the following, the first portion will be referred to as the disposable portion and the second portion as the durable portion. However, this is for discussion purposes only, as both portions may be made to be durable portions or disposable portions. The disposable portion includes a magneto-sensitive element coupled to a wall of a fluid chamber. A time-varying magnetic field is created near the magneto-sensitive element of the disposable portion using an actuator positioned on the durable portion. The time-varying magnetic field causes the magneto-sensitive element to reciprocate between a first position and a second position. The movement of the magneto-sensitive element causes a membrane coupled to the wall of the fluid chamber of the disposable portion to reciprocate, thereby pumping a fluid through the fluid chamber.

In certain embodiments, the actuator includes a first electromagnetic coil through which an electric current of time-varying amplitude is passed to generate the time-varying magnetic field. A control section controls the flow of electric current through the first electromagnetic coil to achieve a desired time-varying magnetic field.

In certain embodiments, the membrane comprises a resilient material. When the magnetic field is turned on, the fluid chamber increases in volume due to the movement of the magneto-sensitive element in response to the time-varying magnetic field. When the magnetic field is turned off, resiliency of the resilient membrane restores the volume of the fluid chamber back to the resting volume. In general, the minimum and the maximum strengths of the time-varying magnetic field are used to control the stroke volume of the pumping operation.

Briefly and in general terms, in certain configurations, a position sensor is provided in close proximity of the membrane to provide a position signal feedback to the control system. The control system is configured to turn off or reduce the magnetic field when the membrane has moved to a certain position. Such a position feedback system helps avoid potentially abrasive contact between the membrane and the pumping system.

These and other features are described in greater detail below. While the description below assumes that generation of the time-varying magnetic field is achieved by using electric current, it is understood that other well-known techniques, such as using permanent magnets to time-vary the magnetic field, are also equally applicable.

Figure 1:
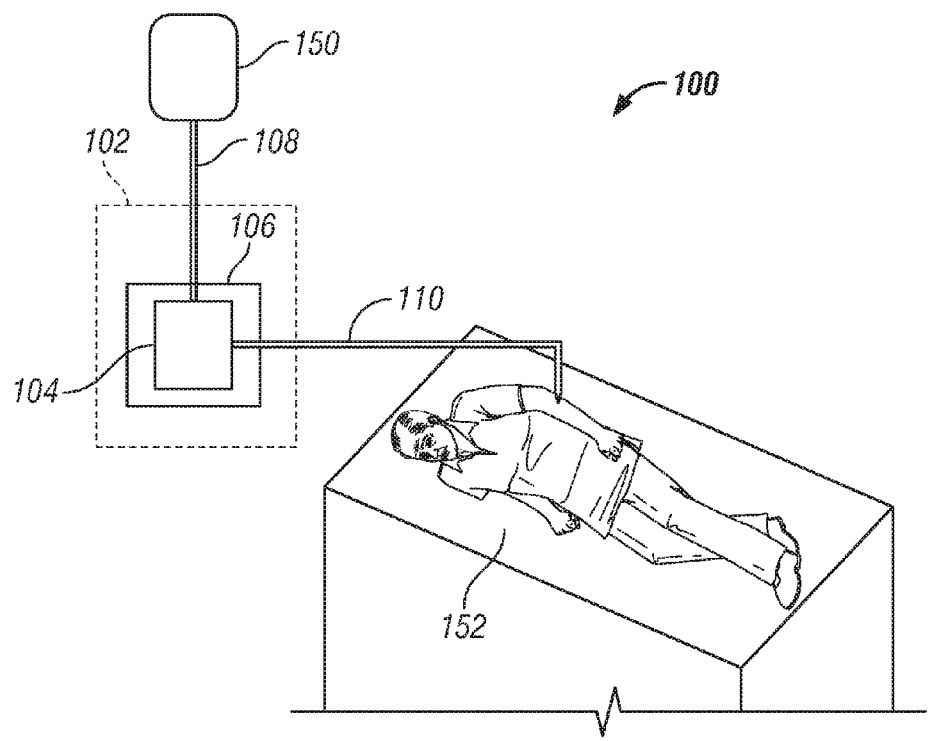
FIG. 1 is a block diagram representation of a patient care system, in accordance with certain embodiments of the present disclosure.

FIG. 1 illustrates a patient care system 100. The patient care system 100 includes a fluid pump apparatus 102 configured to deliver a fluid from a fluid source 150 to a fluid output 152. In the depicted configuration of FIG. 1, the fluid output 152 is provided to a patient. In certain configurations, fluid output 152 is connected to other patient care equipment or a test equipment in a laboratory. The fluid pump apparatus 102 comprises a durable portion 106 (e.g., a fluid pump) and a disposable portion 104 (e.g., a disposable intravenous fluid delivery set). In certain configurations, the fluid pump apparatus 102 comprises a contactless fluid pumping mechanism, such as a magnetically coupled pumping mechanism further described below.

Figure 2:
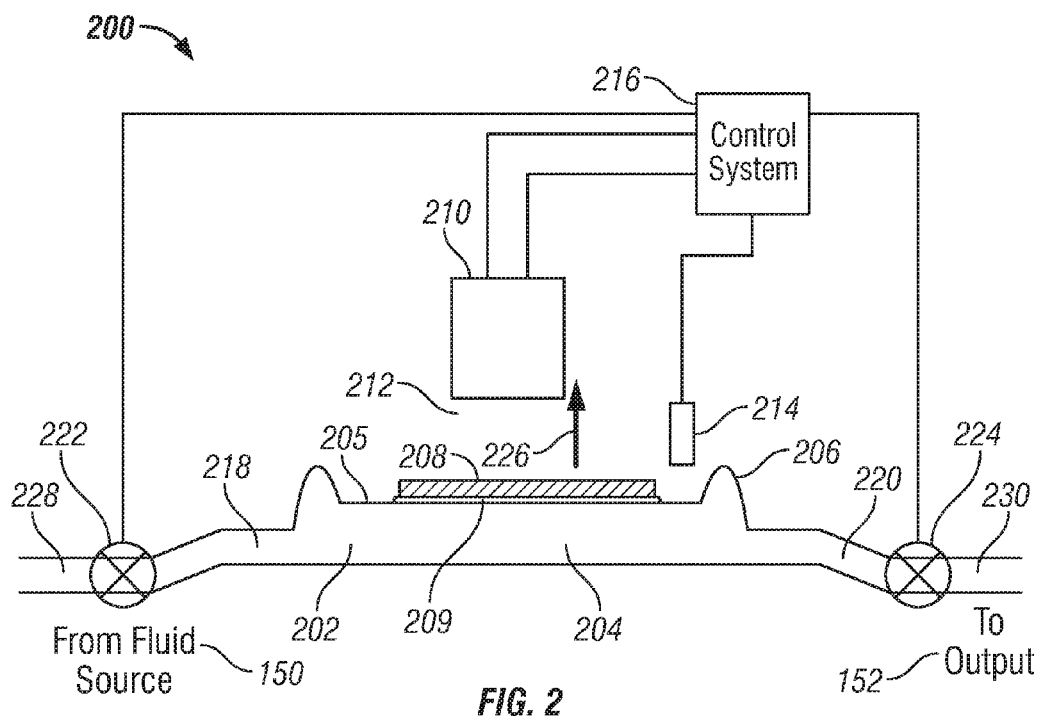
FIG. 2 is a diagrammatic representation of a magnetically coupled pumping mechanism (MCPM) apparatus, in accordance with certain embodiments of the present disclosure.

FIG. 2 is a diagrammatic representation of a magnetically coupled pumping mechanism (MCPM) 200, which forms a portion of a fluid pump apparatus 102 in accordance with certain configurations of the present application. The MCPM 200 includes a fluid chamber 202 having an internal cavity 204 and a wall 205. The wall 205 comprises a membrane 206. A magneto-sensitive element 208 is coupled to the membrane 206. In certain configurations, the physical coupling between the magneto-sensitive element 208 and the membrane 206 comprises an adhesive layer 209. The adhesive layer 209 comprises one of several well known commercially available glues and adhesive fasteners.

An actuator 210 is positioned near the magneto-sensitive element 208 with an air gap 212 separating the actuator 210 from the magneto-sensitive element 208. In certain embodiments, a position sensor 214 is positioned in the proximity of membrane 206. The actuator 210 and the position sensor 214 are communicatively coupled to a control system 216. In certain configurations, the actuator 210 is positioned on the durable portion 106. In certain configurations, the control system 216 is positioned on the durable portion 106. In certain configurations, the fluid chamber 202 and the magneto-sensitive element 208 are positioned on the disposable portion 104.

The fluid chamber 202 further comprises an input port 218 and an output port 220. The input port 218 is coupled to an input fluid line 228 via an input valve 222. The output port 220 is coupled to an output fluid line 230 via an output valve 224. Valves 222, 224 are configured to selectively fluidly connect the fluid chamber 202 with the input fluid line 228 and the output fluid line 230, respectively. In certain configurations, the opening and closing of valves 222, 224 is controlled by the control system 216, to achieve pumping through the fluid pump apparatus 102, as further described below. The input fluid line 228 is in fluid connection with the fluid source 150 (see FIG. 1) and the output fluid line is in fluid connection with the fluid output 152 (see FIG. 1).

The actuator 210 is configured to contactlessly induce a reciprocating movement of the membrane 206 by application of a time-varying magnetic field to the magneto-sensitive element 208. The air gap 212 is provided to have a sufficient clearance to permit unhindered reciprocating movement of the magneto-sensitive element 208 in the direction of the arrow 226. The reciprocating movement of the membrane 206 facilitates pumping of a fluid through the fluid chamber 202, as further explained below.

Figure 3A:
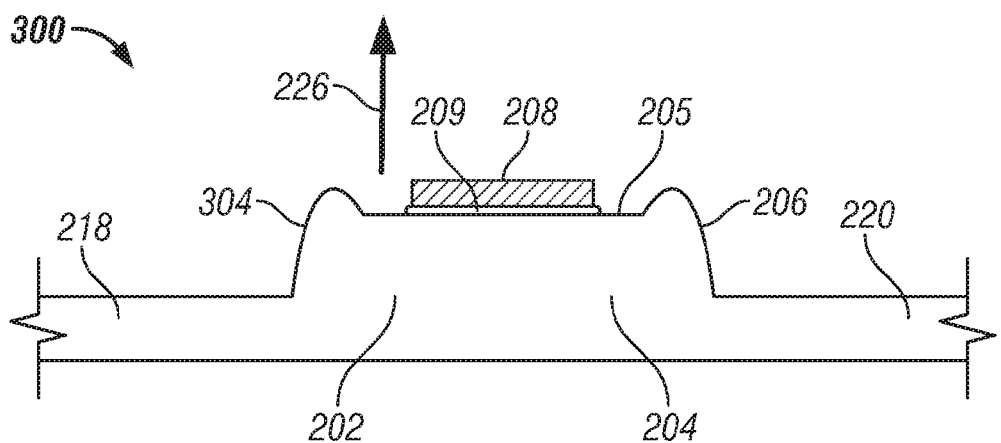
FIGS. 3A, 3B and 3C are diagrammatic representations of positions of a membrane, in accordance with certain embodiments of the present disclosure.
Figure 3B:
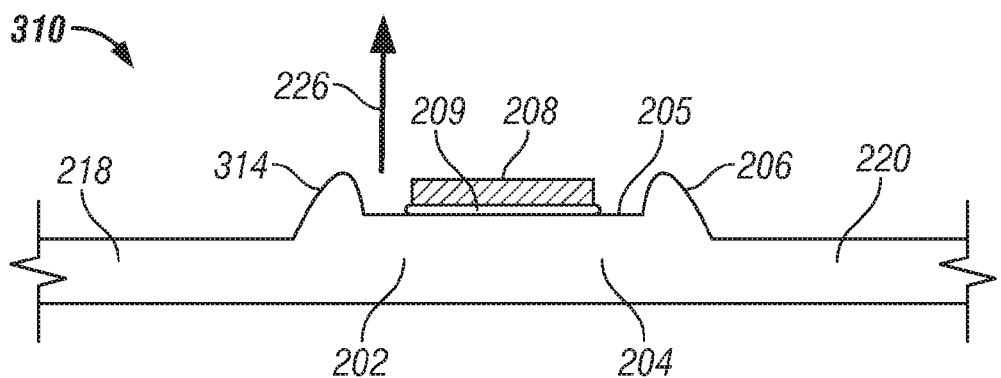
Figure 3C:
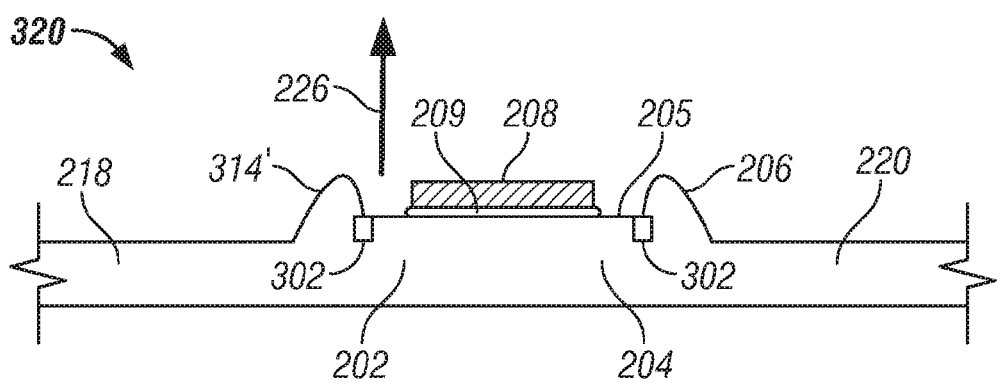

Referring now to FIGS. 3A, 3B and 3C, diagrammatic representations of positions of the magneto-sensitive element 208 and the membrane 206 during the pumping operation are depicted. Movement of the membrane 206 between different positions is achieved by exertion of a magnetic field of varying intensity on the magneto-sensitive element 208 in the direction of arrow 226.

FIG. 3A depicts a configuration 300 wherein the membrane 206 is in a first position 304 in which the internal cavity 204 has a first volume. The membrane 206 is in the first position 304, for example, when the actuator 210 has exerted a maximum magnetic field flux density, attracting the magneto-sensitive element 208 towards the actuator 210, in the direction of the arrow 226. The fluid chamber 202 is held in its position and as a whole is prevented from stretching or moving toward the actuator 210 under magnetic force because of rigidity and weight of the fluid chamber 202. Thus, outward movement of the magneto-sensitive element 208 causes only the membrane 206 to expand towards the actuator 210. The expanding (outward) movement of the membrane 206 in the direction of the arrow 226 results in an increased volume of the internal cavity 204 of the fluid chamber 202. In certain configurations, the magneto-sensitive element 208 and the portion of the wall 205 immediately adjoining the magneto-sensitive element 208 flex to allow an outwardly convex bulging of the magneto-sensitive-element 208, thereby resulting in an increased volume of the internal cavity 204.

FIG. 3B depicts a configuration 310 wherein the membrane 206 is in a second position 314 in which the internal cavity 204 has a second volume. The membrane 206 is in the second position 314, for example, when the actuator 210 has exerted a magnetic field of a second flux density on the magneto-sensitive element 208. With the membrane 206 in the second position 314, the internal cavity 204 has a second volume that is less than the first volume. In certain configurations, when the membrane 206 is in the second position 314, the magneto-sensitive element 208 is substantially planar. The second flux density, for example, corresponds to zero magnetic field (i.e., when the magnetic field created by the actuator 210 is turned off). In other words, in certain embodiments, configuration 310 depicts the position of the membrane 206 when the actuator 210 is not applying any magnetic force to the magneto-sensitive element 208.

FIG. 3C depicts a configuration 320 wherein the membrane 206 is in the position 314', similar to the position 314 depicted in FIG. 3B. In configuration 320, additional stopping elements 302 are provided on the inside of the fluid chamber 202. The stopping elements 302 are, for example, protrusions or bars in the wall 205 to limit inward movement of the membrane 206 in the direction opposite to the arrow 226. While one exemplary embodiment in which stopping elements 302 are placed near the input port 218 and the output port 220 is depicted in FIG. 3C, it is understood that several other placements and shapes of the stopping elements 302 are possible. Furthermore, a different number of stopping elements (e.g., one or three or more) are also possible.

Still referring to FIG. 3C, when the magneto-sensitive element 208 and the membrane 206 are in the position depicted in FIG. 3A and the actuator 210 changes the exerted magnetic field to the second flux density (e.g., turns off the magnetic field or reduces the magnetic field), the magneto-sensitive element 208 and the membrane 206 begin to pull back in the direction opposite to the arrow 226. The pullback is caused, for example, by resiliency of the material of the membrane 206. During the pullback, the stopping elements 302 limit the travel of the membrane 206 to the position 314' depicted in FIG. 3C. The limiting prevents the pullback from "over shooting," i.e., causing the volume of internal cavity 204 to reduce below the first volume. The stopping elements 302 also limit the pullback of the membrane 206, thereby dampening possible oscillations in the membrane 206 during the pullback, which may result in an undesired turbulence in the fluid being pumped through the fluid pump apparatus 102.

Figure 4:
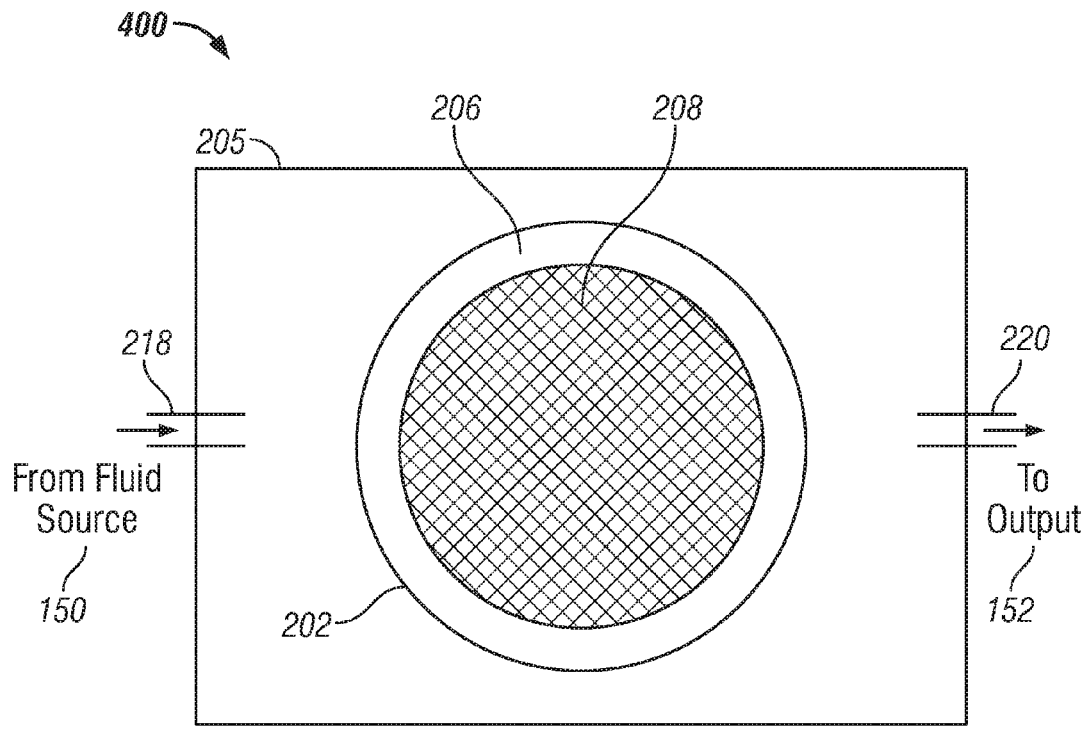
FIG. 4 is a diagrammatic representation of a top level view of a membrane, in accordance with certain embodiments of the present disclosure.

FIG. 4 is a diagrammatic representation of a top view 400 of the fluid chamber 202, in accordance with certain configurations of the present disclosure. In the depicted configuration, the wall 205 is rectangular. In certain configurations, the rectangular shape is chosen to match, for example, the shape of a disposable cassette used in the fluid delivery system 100. The membrane 206 is circular and embedded with the wall 205 to form a portion of the wall 205. While the circular shape of the membrane 206 may be useful in evenly spreading the stretching force at the joint between the membrane 206 and the wall 205, other shapes (e.g., rectangular) are also possible. The magneto-sensitive element 208 is coupled to the membrane 206 towards the center of the membrane 206 with respect to the wall 205. The input port 218 and the output port 220 are provided for transferring fluid through the fluid chamber 202. In certain configurations, the wall 205 comprises a structurally rigid material such as hard plastic. The structurally rigid wall 205 advantageously makes it easier to handle the fluid chamber 202 during initial placement and subsequent removal from the durable portion 106.

Still referring to FIG. 4, in certain configurations, the membrane 206 comprises a resilient material. As explained in more detail below, in certain configuration, the resiliency of the membrane 206 is used to achieve reciprocation of the membrane 206. For example, in certain configurations, the pullback of the membrane 206 from the first position 304 to the second position 314 is due to resiliency of the membrane 206.

Alternatively, the membrane 206 comprises a flexible, elastic material, such as Mylar®. The flexibility of the membrane 206 is selected to allow many repetitions (e.g., up to a million or more) of the reciprocating movement of the membrane 206 without causing elastic fatigue in the membrane 206. While in the depicted configuration of FIG. 4, the membrane 206 and the magneto-sensitive element 208 are circular in shape, the membrane 206 and the magneto-sensitive element 208 need not have the same shape. Several different shapes are possible for the membrane 206 and the magneto-sensitive element 208, suitable to fit with geometries of the fluid chamber 202 and the durable portion 106. The magneto-sensitive element 208 may also comprise multiple separate portions. A multi-portion configuration of the magneto-sensitive element 208 offers the advantage of covering a larger surface area of the membrane 206, while utilizing the same amount of magneto-sensitive material, compared to a single magneto-sensitive element configuration.

Figure 5:
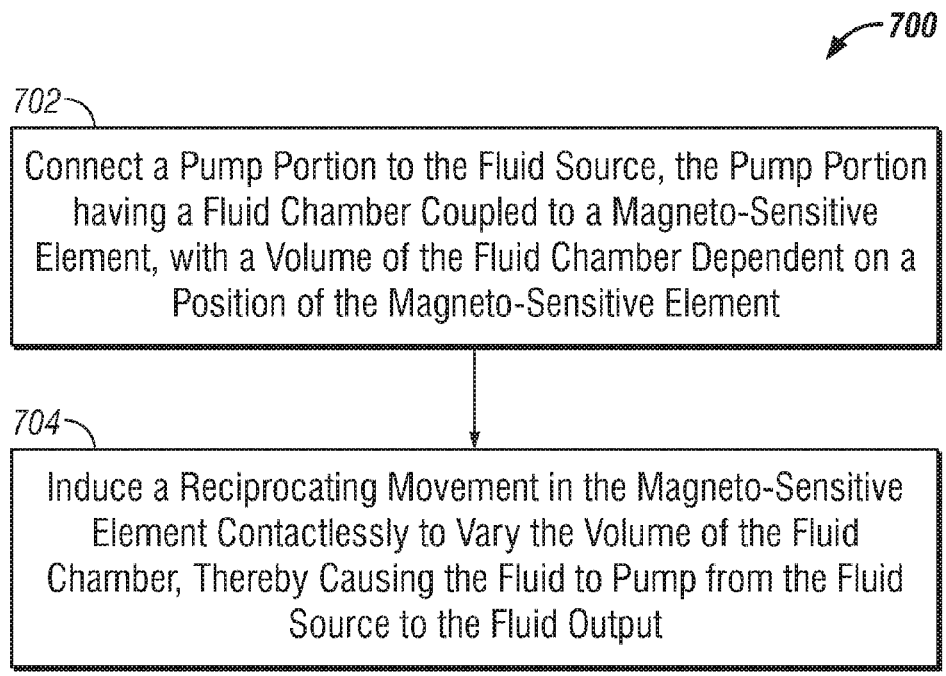
FIG. 5 is a flow chart representation of a method of pumping fluid, in accordance with certain embodiments of the present disclosure.

FIG. 5 is a flow chart representation of a method 700 of pumping fluid from a fluid source to a fluid output, in accordance with certain configurations disclosed herein. At operation 702, a pump portion is connected to the fluid source, the pump portion having a fluid chamber coupled to a magneto-sensitive element, with a volume of the fluid chamber dependent on a position of the magneto-sensitive element. At operation 704, a reciprocating movement is contactlessly induced in the magneto-sensitive element to vary the volume of the fluid chamber, thereby causing the fluid to pump from the fluid source to the fluid output. In certain embodiments, the pumping is performed in pumping cycles.

Figure 6:
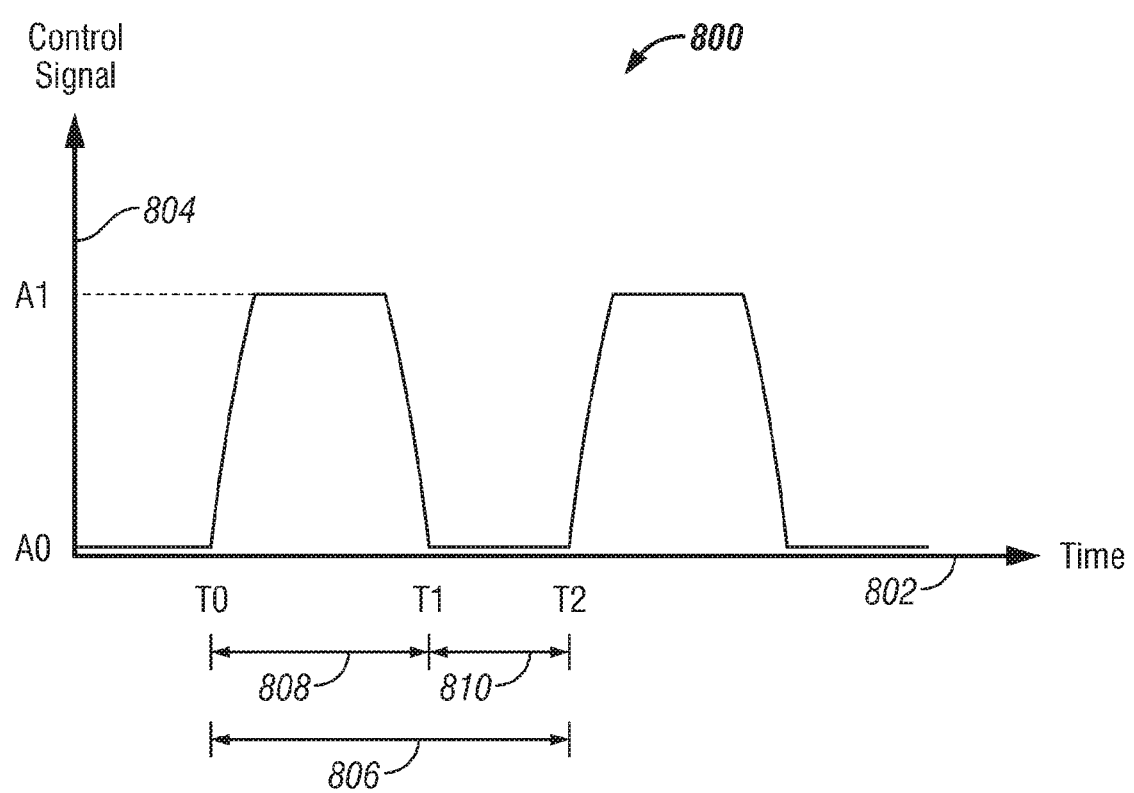
FIG. 6 is a graphical representation of a signal for controlling fluid pump operation, in accordance with certain embodiments of the present disclosure.

With reference to FIG. 6, the operation of pumping the fluid in pumping cycles is depicted as follows. FIG. 6 is a plot of a signal generated by the control system 216 for controlling fluid pump operation, in accordance with certain configurations disclosed herein. The horizontal axis 802 represents linearly increasing time and the vertical axis 804 represents magnitude of a control signal (e.g., current through an electromagnetic coil of the actuator 210 or the flux density of the corresponding electromagnetic field generated by the actuator 210). The pumping operation comprises repetitions of pump cycles 806 having an input phase 808 and an output phase 810. During the input phase 808, beginning at time T0, the output valve 224 is fluidly closed, the input valve 222 is fluidly open and a magnetic field of a first flux density A1 is applied to the magneto-sensitive element 208. As a result, the fluid chamber 202 expands in volume to a first volume, thereby allowing the fluid from the input fluid line 228 to enter the fluid chamber 202. During the output phase 810, beginning at time T1, the output valve 224 is fluidly open, the input valve 222 is fluidly closed and a magnetic field of a second flux density A0 is applied to the magneto-sensitive element 208, allowing the fluid chamber 202 to pull back, thereby causing a certain amount of fluid to be expelled from the fluid chamber 202 to the output fluid line 230. The input/output phases 808, 810 are repeated, as desired, beginning at time T2.

Still referring to FIG. 6, a single pumping cycle 806 spans the time period between times T0 and T2, comprising the input phase 808 between times T0 and T1 and the output phase 810 between times T1 and T2. In certain configurations, the input phase 808 and the output phase 810 have substantially identical durations. In certain other configurations, the input phase 808 and the output phase 810 have different durations. For example, in certain configurations, the input cycle 808 is shorter than the output cycle 810, which has a longer duration to ensure laminar fluid flow downstream from the output port 220. In certain configurations, the pumping cycle 806 is about 300-400 milliseconds long, i.e., a repetition rate of 2 to 3 pumping cycles per second.

Still referring to FIG. 6, in certain configurations, the periodicity of the pump cycle 806 is pre-selected based on a desired flow rate. For example, for the same amount of fluid displacement per pumping cycle 806, a shorter duration pump cycle 806 results in a higher flow rate of pumping through the fluid chamber 202. Similarly, larger differences between A0 and A1 generally result in a higher volume of the fluid being pumped in each pump cycle 806.

In certain configurations, the control system 216 uses a position signal received from the position sensor 214 to decide the time T1 at which the magnetic field is transitioned from A1 to A0. For example, when the position signal from the position sensor 214 indicates that the membrane 206 has reached the desired maximum displacement (i.e., the volume of the internal chamber 202 has reached a desired maximum value), the control system 216 causes the control signal to transition from the value A1 to A0. As a result of the change in the value of the control signal (e.g., reduction in flux density of the exerted magnetic field), the membrane 206 resiles from the position 304 depicted in FIG. 3A to the position 314 depicted in FIG. 3B. In certain configurations, the control system 216 is programmable such that the magnitude of A0 and A1 can be changed "on the fly." The changed magnitudes of the signals A0 and A1 result in a changed amount of fluid pumped per pumping cycle 806. For example, a reduced value of the difference between A1 and A0 results in a reduced amount of fluid being pumped in one pumping cycle 806. In certain configurations, the control system 216 is also programmable to change the time period of the pumping cycle 806, thereby causing a change to the flow rate.

Figure 7:
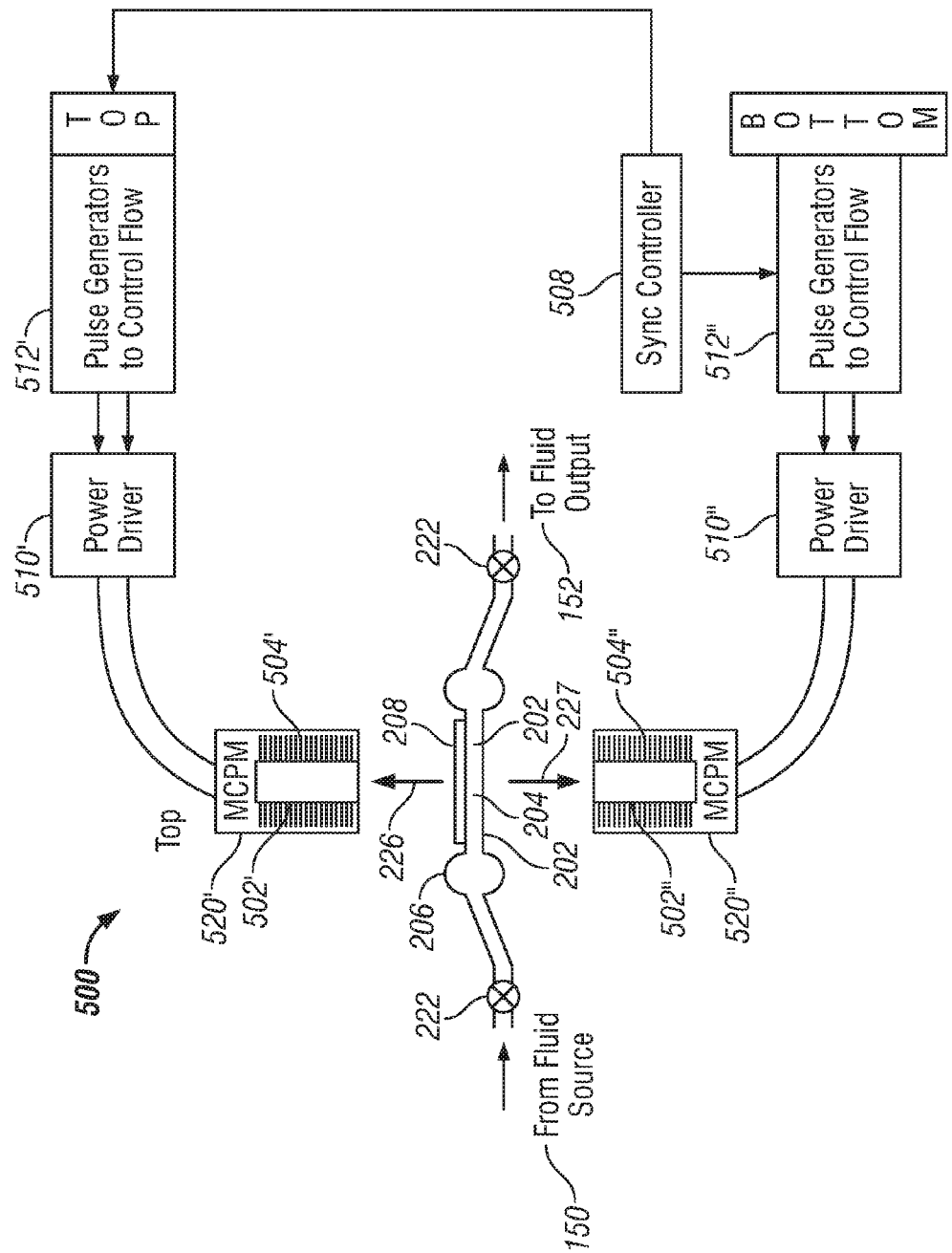
FIG. 7 is a diagrammatic representation of a magnetically coupled pumping mechanism (MCPM) apparatus, in accordance with certain embodiments of the present disclosure.

FIG. 7 is a diagrammatic representation of an MCPM apparatus 500, in accordance with certain configurations of the present disclosure. Compared to the configuration 200 depicted in FIG. 2, wherein the time-varying field is generated by one actuator 210, the MCPM apparatus 500 comprises two portions: a top actuator 520' and a bottom actuator 520". The terms "top" and "bottom" refer to an arbitrary frame of reference used in the depiction of FIG. 6. During operation, the orientation of the actuators 520', 520" depends on the orientation of the disposable portion 104 in the durable portion 106.

The top and bottom actuators 520', 520" are operated in synchronization with each other and under control of a Sync Controller 508. The top actuator 520' comprises an electromagnetic core 502' and an electric conductive coil 504' such that passing current through the coil 504' generates a magnetic field that attracts the electro-magnetic element 208 in the direction of the arrow 226. The bottom actuator 520" comprises an electromagnetic core 502" and an electric conductive coil 504" such that passing current through the coil 504" generates a magnetic field that attracts the electro-magnetic element 208 in the direction of the arrow 227. The Sync Controller 508 controls the operation of pulse generators 512', 512" configured to provide electric current generation signals to the power drivers 510', 510". The power drivers 510', 510" control the amount of current flowing through the coils 504', 504" respectively.

The Sync Controller 508 controls the current flowing through the coils 504', 504"; thereby controlling the magnetic flux density of the time-varying magnetic fields generated by the actuators 520', 520". The Sync Controller 508 achieves pumping of fluid through the fluid chamber 202 by repetitively reciprocating the magneto-sensitive element 208 in the direction of the arrows 226, 227. The Sync Controller 508 achieves movement of the magneto-sensitive element 208 in the direction of arrow 226 when the attractive force of the magnetic field generated by the coil 504' over the magneto-sensitive element 208 is greater than that of the magnetic field generated by the coil 504", and vice versa. For example, in certain configurations, the Sync Controller 508 simultaneously turns current on in one of the coils 504', 504" and turns the current off in the other one of the coils 504', 504" to achieve transition between positions 304 and 314 (see FIGS. 3A and 3B) of the magneto-sensitive element 208.

The use of two magnetic fields is advantageous when the membrane 206 comprises an elastic material that is not sufficiently resilient to resile back to its resting position (e.g., position 314 depicted in FIG. 3B) when the magnetic field generated by the actuator 502' is reduced or is turned off. In such configurations, the Sync Controller 508 causes the magneto-sensitive element 208 to move in the direction of arrow 227 by generating a magnetic field using the actuator 520". The two-actuator MCPM apparatus 500 is therefore suitable for use in a durable portion 106, when the disposable portion 104 is expected to include fluid chamber 202 comprising elastic (but not adequately resilient) membranes 206.

Figure 8:
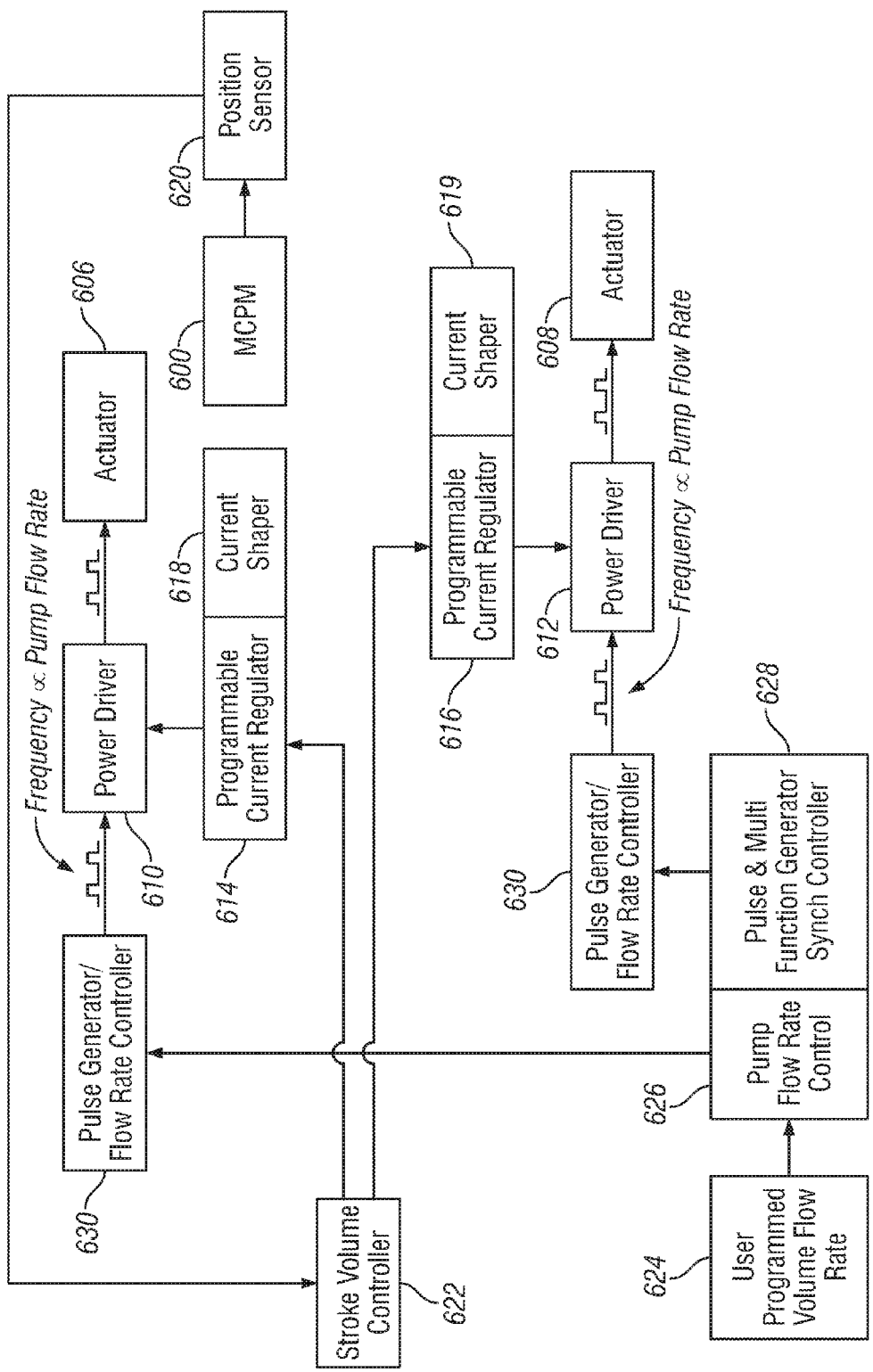
FIG. 8 is a block diagram representation of a pump control system, in accordance with certain embodiments of the present disclosure.

FIG. 8 is a block diagram of an exemplary control system 216 for controlling fluid pump configuration 200 or 500. A magnetically coupled pumping mechanism 600 is controlled by a "pull-up" actuator 606 and a magnetically controlled "pull-down" actuator 608. The actuator 606 is provided to create the pull-up magnetic force (e.g., similar to the actuator 520' depicted in FIG. 7) and the bottom actuator 608 is provided to create the pull-down magnetic force (e.g., similar to the actuator 520" depicted in FIG. 7). A power driver 610 supplies electrical power to the actuator 606 and a power driver 612 supplies electrical power to the actuator 608. A first programmable current regulator 614 controls the operation of the power driver 610. A second programmable current regulator 616 controls the operation of the power driver 612. The programmable current regulators 614, 616 include electric current shapers 618, 619, which produce a time varying pattern of electric current proportional to the magnetic force desired for the operation of the MCPM 600. A High frequency current chopper module (e.g., lowpass filters, not shown) smoothes out "glitches" or high frequency noise in the current signal. A position sensor 620 produces a position feedback signal (e.g., position of the membrane 206), which is utilized by a stroke volume controller module 622 for controlling the magnetic force generated by the top and the bottom electromagnets 606, 608. The module 622 provides a feedback signal to the current regulators 614, 616 to control the strength of the magnetic field exerted upon the magneto-sensitive element 208.

A module 624 allows a user to input a programmable volume flow rate. This can be done through a user interface or automatically through networked control systems. A pump flow rate control module 626 translates the user input into control signals for adjusting pulse timings (e.g., the pumping cycle 806) and pulse intensities (e.g., values of A0 and A1), thereby controlling the time variability and the strength of the magnetic field applied to the magneto-sensitive element 208. A pulse and multifunction synch controller 628 is provided to control the start/end times of control signals (e.g., current into the actuators 606, 608). Pulse generator/flow rate controller modules 630 are provided to control a flow rate of the fluid pumped through MCPM 600 by controlling the period of the pumping cycle 806 using a control input from the pump flow rate control module 626.

The magnetic force (F) applied by an electromagnetic field is defined by the flux density (B) of the magnetic field and the flux density is defined by the current through the EM coil. See Eq (1).

$$B = \frac{\mu_0 \cdot \mu_r \cdot i_{EM} \cdot N}{l} \qquad \text{Eq (1)}$$

In Eq (1), N is the number of turns of wire in the electromagnetic (EM) coil,
$\mu_0$ is the permeability of free space and is $1.25664 \times 10^{-5}$ Newtons/Amps² (N/A²)
$\mu_r$ is relative permeability of EM coil core, and
l is the effective length of EM coil. The magnetic force F is given by $$F = \frac{B^2 \cdot S}{\mu_0} \qquad \text{Eq (2)}$$

In Eq (2), S is the surface area of the magneto-sensitive element 208.

Eq (1) and Eq (2) assume a zero (or infinitesimal) gap between the magneto-sensitive element 208 and an electromagnetic coil of the actuator 210. As the gap increases, the relationship between the force F and the width of the air gap 212 (FIG. 2) is in general a function of the material of magneto-sensitive element 208. For example, empirical experimentation by the inventor has shown an approximately exponential relationship between the force F and the air gap 212, as discussed next.

Figure 9:
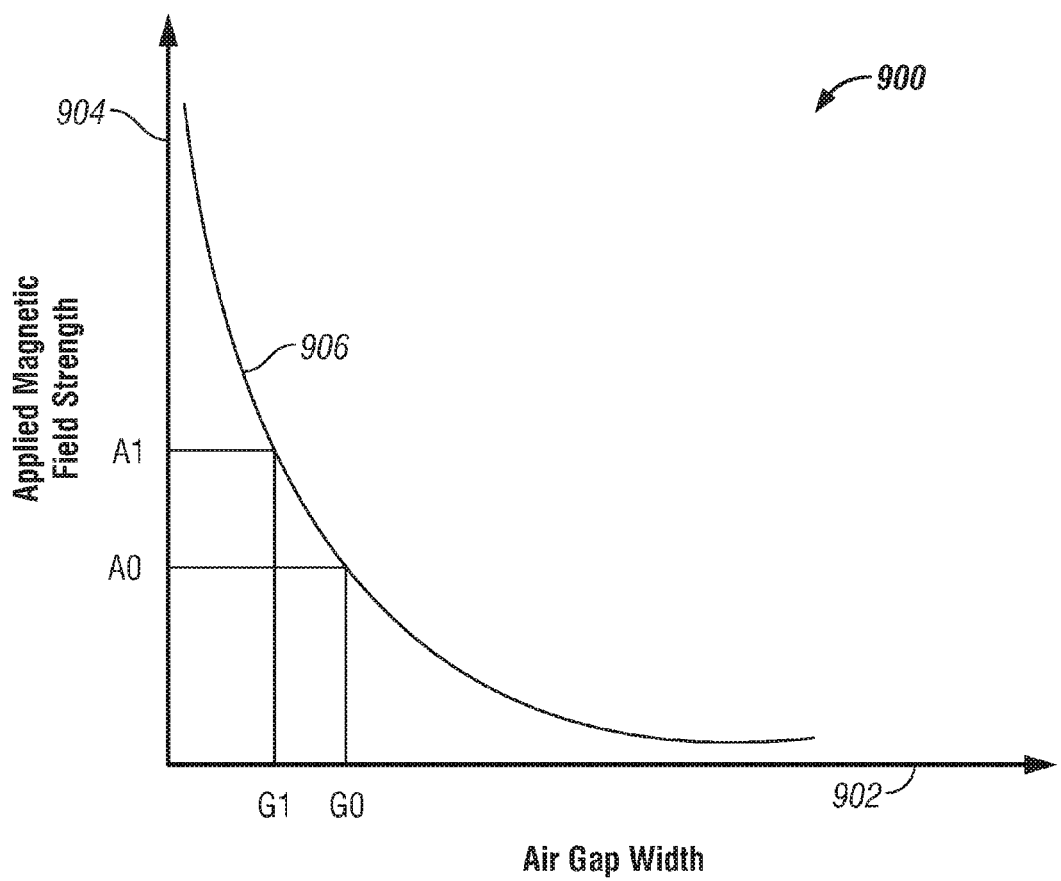
FIG. 9 is a graphical representation of a functional relationship between a magnetic field density and an air gap between a membrane and an actuator, in accordance with certain embodiments of the present disclosure.

FIG. 9 is a plot 900 of an exemplary functional relationship 906 between a flux density of the applied magnetic field strength plotted on the vertical axis 904 and the width of the air gap 212 plotted on the horizontal axis 902, in accordance with certain configurations disclosed in the present disclosure. During pumping operation, the point (G1, A1) represents, for example, position 304 depicted in FIG. 3A, wherein the membrane 206 is closest to the actuator 210. The point (G0, A0) represents, for example, position 314 depicted in FIG. 3B, wherein the membrane 206 is farthest from the actuator 210. It will be appreciated that the amount of fluid pumped in one pumping cycle 806 ("stroke volume") is proportional to a difference between gaps G0 and G1. In certain configurations, the stroke volumes are thus controlled to be as large or as small as needed to meet IV flow volume requirements at various flow volume rates, simply by controlling the flux densities A1 and A0.

In certain configurations, the waveform controlling the flux density generated by the actuator 210 can be programmed to have any desired wave function, such as, a pulse, an impulse, a sinusoid, a sawtooth, or a combination of these functions. In certain configurations, a programmable current function Ipgm(t) is used to generate a programmable current function $i_{EM}$ to control inductive voltage swings produced by rapid changes in current through an inductor $L_{EM}$, a diode in parallel with the inductor $L_{EM}$ or an RC snubber circuit in parallel to the inductor $L_{EM}$. In certain configurations, an RC circuit is used to allow the current through $L_{EM}$ to decay rapidly. In certain configurations, to achieve smooth time variability of the magnetic field, a snubber is used to absorb voltage spikes across the inductor $L_{EM}$. The programming of the waveform is readily performed by one of skill in the art, depending on the desired wave function.

Figure 10:
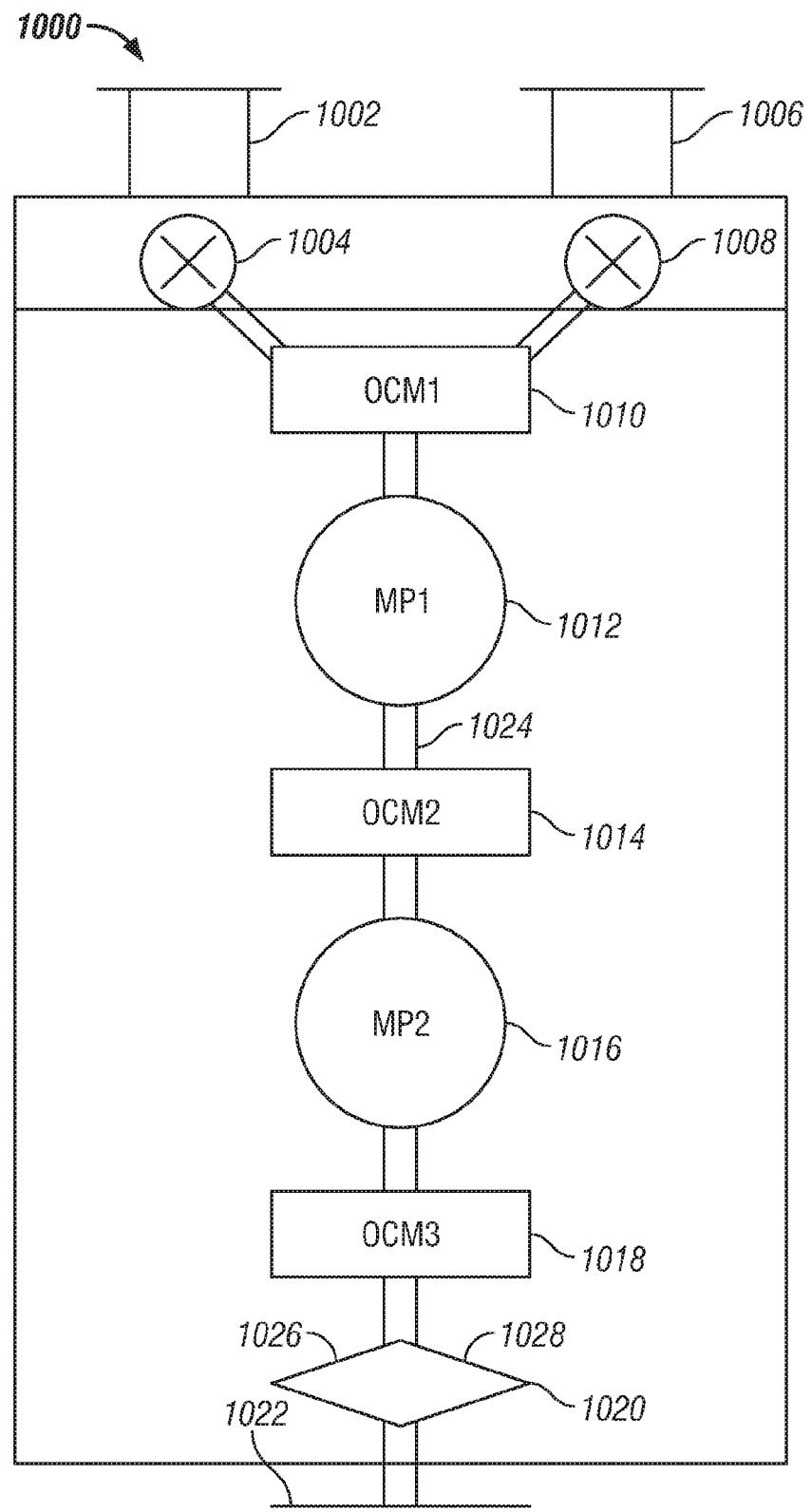
FIG. 10 is a block diagram representation of a contactless infusion pump, in accordance with certain embodiments of the present disclosure.

FIG. 10 is a diagrammatic representation of a contactless infusion pump 1000, in accordance with certain embodiments of the present disclosure. The contactless infusion pump 1000 includes two input fluid lines 1002 and 1006, fluidly connected to the respective fluid containers (not shown in FIG. 10). An inlet valve 1004 and an inlet valve 1008 are provided to control fluid connection between input fluid lines 1002, 1006 and a first occluder OCM1 1010. A fluid line 1024 in the downstream direction (i.e., towards the fluid output 1022) from occluder 1010 is provided to carry fluid mixture of fluid lines 1002, 1006. The following pump elements are provided in the downstream direction from the occluder 1010: a first contactless pump section MP1 comprising a magneto-sensitive element 1012, a second occluder OCM2 1014, a second contactless pump section MP2 comprising a magneto-sensitive element 1016, a third occluder OCM3 1018, and a magnetic closure device 1020.

An external control system (not shown in FIG. 10) is provided to control the pumping of fluid through the contactless infusion pump 1000 in a manner similar to the control of a finger-type peristaltic infusion pump. In certain configurations, the external control system achieves the pumping as follows: First, operate occluder 1010 to fluidly isolate downstream components of the contactless infusion pump 1000 from the fluid lines 1002, 1006. Next, operate valves 1004, 1008 to allow fluid from fluid lines 1002, 1006 to mix together at the occluder 1010. Next, operate valves 1004, 1008 to fluidly disconnect fluid lines 1002, 1006 from the occluder 1010. Next, operate the occluder 1010, the occluder 1014, the occluder 1018 and the pump section MP1 to pump the fluid from the occluder 1010 towards the pump section MP2, but not further downstream from the occluder 1018. Next, fluidly disconnect the upstream portion of the fluid line 1024 at the occluder 1014, operate the occluder 1018 and operate the pump section MP2 to pump fluid downstream to fluid output 1022.

The magnetic closure device 1020 ensures that the disposable portion 104 of a fluid delivery system is fluidly sealed from downstream fluid line, thereby avoiding unwanted downstream discharge of fluid when the disposable portion 104 is not in use. In certain configurations, the magnetic closure device 1020 comprises magneto-sensitive areas 1026 and 1028 such that when a disposable portion 104 is taken out of the durable portion 106, the fluid line 1024 is closed due to the normal (or unstressed) shape and position of the magneto-sensitive areas 1026 and 1028. When the disposable portion 104 is inserted in the durable portion 106, the external control system exerts a magnetic field on the magneto-sensitive areas 1026 and/or 1028 to pull the areas 1026, 1028 apart, thereby allowing fluid to pass through the fluid line 1024. It should be noted that the magnetic closure device 1020 is usable with any other infusion pump, independent of other contactless pumping elements depicted in FIG. 10. Accordingly, certain disposable portions 104 in accordance with configurations disclosed herein comprise the closure means 1020, without the contactless pumping sections 1012, 1016.

While the contactless fluid pump 1000, depicted in FIG. 10, is a two-input, one-output pump, it will be appreciated that the contactless pumping schemes described above are applicable to other configurations with a different number of input fluid lines (e.g., one or three or more input fluid lines). Also, while the contactless fluid pump 1000 is described to have three occluders and two contactless pump sections, several variations in the positioning of occluders, valves and magneto-sensitive elements are possible. For example, in certain configurations, the occluder 1010 is omitted and fluid connection/disconnection is managed by operating valves 1004, 1008 only.

In certain embodiments, the magneto-sensitive elements 1012, 1016 are same as the magneto-sensitive element 208 described herein. Furthermore, while the magneto-sensitive elements 1012, 1016 are depicted in FIG. 10 as circular disjoint portions, various shapes of the magneto-sensitive elements 1012, 1016 are possible, as discussed previously with respect to the magneto-sensitive element 208. In certain embodiments, the contactless pumping operation of each section MP1 and MP2 is similar to that of the MCPM 200.

It will be appreciated that the present disclosure provides methods and apparatuses for contactless fluid pumping in a patient care system. By avoiding mechanical contact, the contactless pumping schemes described herein eliminate or substantially reduce the noise generated by mechanical pumps. The noiseless operation of the disclosed fluid pumps therefore makes the disclosed fluid pumps especially suitable for use in noise sensitive areas such as a neonatal unit or an intensive care unit.

Furthermore, stroke volume periodicity of the pumping cycle is adjustable on-the-fly, thereby making it easier for a caregiver to control the operation of the fluid pump apparatus without having to stop an ongoing infusion to make changes to these parameters.

In addition, because the pumping operation is frictionless, the fluid pump apparatuses disclosed herein can be operated for longer durations compared to conventional pumps (e.g., four days or more), without the need to replace parts or batteries. Certain disclosed pump configurations also perform peristaltic pumping, such as a multi-finger pump, using contactless pumping sections.

The embodiments of the disclosure have been generally described in the context of patient care systems. However, the disclosure of the present application is applicable to fluid pumping in contexts other than patient care, and relates to pumping of fluids in general.

Although embodiments of the present disclosure have been described and illustrated in detail, it is to be clearly understood that the same is by way of illustration and example only and is not to be taken by way of limitation, the scope of the present invention being limited only by the terms of the appended claims.

What is claimed is:

1. A fluid pump apparatus comprising:
   a housing configured to accept a disposable portion having an internal cavity with an input port and an output port, a movable wall having a variable position that includes a first position at which the internal cavity has a first volume and a second position at which the internal cavity has a second volume, and a planar magneto-sensitive element coupled to the movable wall and oriented perpendicular to a direction of motion between the first and second positions at all positions of the movable wall between the first and second positions;
   a stopping element disposed in the housing and configured to prevent a volume of the internal cavity formed by the movable wall from reducing below the second volume;
   a position sensor coupled to the housing and configured to detect the position of the movable wall and provide a position signal;
   a first actuator and a second actuator coupled to the housing and positioned within the housing such that the magneto-sensitive element is disposed between the first and second actuators when the disposable portion is accepted, wherein the first actuator is configured to selectably create a first magnetic field to attract the magneto-sensitive element so as to draw the movable wall toward the first position and the second actuator is configured to selectably create a second magnetic field to attract the magneto-sensitive element so as to draw the movable wall toward the second position;
   and
   a controller communicatively coupled to the position sensor and the first and second actuators, the controller configured to receive the position signal and cause the first actuator to attract the magneto-sensitive element until the movable wall reaches the first position during an input cycle lasting for a first period of time, and then cause the second actuator to attract the magneto-sensitive element until the movable wall reaches the second position during an output cycle lasting for a second period of time, wherein the second period of time is longer than the first period of time to provide a laminar fluid flow downstream from the output port.

2. The fluid pump apparatus of claim 1, wherein:
   the first and second actuators respectively comprise a first electromagnetic coil and a second electromagnetic coil that are configured to create the respective first and second magnetic fields by passage of a constant current through the electromagnetic coil in a single direction during first and second portions, respectively, of a pumping cycle; and
   the controller is further configured to cause the current to flow through only one of the first and second electromagnetic coils at a time.

3. The fluid pump apparatus of claim 1, wherein the movable wall is substantially rigid.

4. The fluid pump apparatus of claim 3, wherein:
   the disposable portion comprises a flexible membrane surrounding and sealingly coupled to the movable wall; and
   the flexible membrane changes shape as the movable wall moves between the first and second positions.

5. The fluid pump apparatus of claim 1, further comprising an input valve coupled between the internal cavity and the inlet port and an output valve coupled between the internal cavity and the output port.

6. The fluid pump apparatus of claim 5, wherein:
   the input valve is open and the output valve is closed when the movable wall is moving toward the first position; and
   the input valve is closed and the output valve is open when the movable wall is moving toward the second position.

7. The fluid pump apparatus of claim 6, wherein the input and output valves are operatively coupled to the controller and opening and closing of the input and output valves are controlled by the controller.

\* \* \* \* \*